United States Patent [19]

Wiese

[11] 4,029,601
[45] June 14, 1977

[54] NOVEL OLIGOMERIZATION CATALYSTS AND THEIR PREPARATION

[75] Inventor: Herbert K. Wiese, Cranford, N.J.

[73] Assignee: Exxon Research and Engineering Company, Linden, N.J.

[22] Filed: Apr. 29, 1975

[21] Appl. No.: 572,654

[52] U.S. Cl. .............................. 252/447; 252/446
[51] Int. Cl.² .................................... B01J 21/18
[58] Field of Search ........................ 252/447, 446

[56] References Cited

UNITED STATES PATENTS

| | | | |
|---|---|---|---|
| 2,407,814 | 9/1946 | Cheney | 252/447 |
| 2,692,261 | 10/1954 | Peters | 252/447 X |
| 2,727,023 | 12/1955 | Evering | 252/447 X |
| 3,317,628 | 5/1967 | Schuck | 252/447 X |
| 3,333,016 | 7/1967 | Schultz | 252/447 X |
| 3,333,017 | 7/1967 | Schuck | 252/447 X |
| 3,356,756 | 12/1967 | Schultz | 252/447 X |

Primary Examiner—Winston A. Douglas
Assistant Examiner—John F. Niebling
Attorney, Agent, or Firm—F. A. Santoro; C. L. Kim

[57] ABSTRACT

Novel oligomerization catalysts comprising cobalt oxide on carbon in admixture with certain other catalyst supports, such as refractory oxides, i.e. alumina, silica alumina and molecular sieves and the like are herein disclosed. The preparation of said novel catalysts is likewise disclosed and the use of said catalysts in propylene oligomerization reactions is hereby described and claimed. The novel oligomerization catalysts are produced by: (a) impregnating activated carbon with a solution containing a cobalt amine complex; (b) treating the impregnated activated carbon at elevated temperatures in order to decompose the cobalt salt to cobalt oxide; and (c) thereafter admixing the so-formed cobalt oxide on carbon with a catalyst support material such as bauxite. In another embodiment, the catalysts may be prepared by impregnating carbon with cobalt nitrate, adding aqueous sodium hydroxide or potassium hydroxide to convert the cobalt nitrate to cobalt hydroxide, extracting with water from the mixture the sodium or potassium nitrate formed, decomposing at high temperatures the cobalt hydroxide to cobalt oxide and thereafter admixing the cobalt oxide on carbon with a catalyst support such as alumina, bauxite, molecular sieves and the like.

2 Claims, No Drawings

4,029,601

NOVEL OLIGOMERIZATION CATALYSTS AND THEIR PREPARATION

BACKGROUND OF THE INVENTION

This invention relates to the oligomerization of alkenes, preferably propylene to linear and slightly branched olefins by employing novel catalysts comprising physical mixtures of cobalt oxide on carbon with certain catalyst support materials such as refractory oxides and molecular sieves. In another embodiment, the invention describes a method of producing said novel catalysts by either of the following two processes, namely, (1) impregnating activated carbon with a solution containing a cobalt amine complex, as hereinafter described, followed by decomposing the cobalt salt to cobalt oxide; or, (2) impregnating carbon with cobalt nitrate, adding aqueous sodium hydroxide or potassium hydroxide at room temperature to convert the cobalt nitrate to cobalt hydroxide, removing the sodium or potassium nitrate with water extraction and decomposing cobalt hydroxide to cobalt oxide a high temperatures. The so-formed cobalt on carbon is thereafter combined with a catalyst support material comprising refractory oxides and/or molecular sieves in order to form the active catalyst system of the instant invention. The use of the novel catalyst compositions in the process described herein permits the polymerization of alkenes such as propylene at mild conditions to yield olefin oligomers rich in linear and slightly branched olefins such that significant amounts of desirable trimers and tetramers are produced. In addition, the use of these novel catalysts in the oligomerization reaction provides a means whereby a broad range of activated carbons such as, for example, petroleum-base activated carbons, can be employed. Moreover, it has been found that the product distribution can be varied by varying the catalyst support.

It is known that cobalt oxide on carbon is a good catalyst for the dimerization of propylene to produce high yields of linear hexenes. The difficulty with employing cobalt oxide on carbon as a catalyst in the prior processes was that in order to have an active catalyst produced, the cobalt oxide had to be prepared by decomposing cobalt nitrate at high temperatures. This decomposition of cobalt nitrate impregnated on the carbon support is hazardous because of the potentially explosive nature of such a mixture. Additionally, other difficulties in the prior art techniques reside in the fact that cobalt oxide on carbon is essentially a dimerization catalyst and therefore does not produce significant amounts of desirable trimers and tetramers.

Typical of the prior art processes and catalysts for olefin oligomerization may be found described in British Pat. No. 1,102,298. This patent teaches the addition of an alkali metal as the promoter to the cobalt activated carbon catalyst; said promoter is said to increase the activity of the catalysts toward olefin oligomerization. The catalysts employed by the patentees are those prepared from cobalt salts and essentially cobalt nitrate is the preferred cobalt salt seen necessary by the patentees to provide an active enough catalyst for olefin oligomerization.

In another British Pat. No. 1,124,766, the preparation of oligomerization catalysts is described which comprises the steps of depositing a nitrate and a cobalt compound on activated carbon, heating the carbon on which the cobalt compound and the nitrate have been deposited until all the nitrate has reacted and heating the carbon in an inert atmosphere at temperatures in the range of 200°–600° C. The patentees of this reference state that it is an essential feature of their invention that at least a part of the total nitrate content of the carbon, prior to the nitrate reaction step being carried out, be supplied by nitrates other than cobalt nitrates and suggest the use of transition metal nitrates for this purpose.

Another prior art process for the preparation of catalysts suitable for olefin oligomerization is described in British Pat. No. 1,151,266. This patent discloses an improved method of making carbon/cobalt catalysts that does not include the necessity of using cobalt nitrate as a source of the cobalt. According to the invention described by these patentees, the process for the production of cobalt/carbon catalyst comprises heating activated carbon onto which cobalt, copper and/or nickel have been introduced by deposition of their salts, other than the nitrates, in a mixture of the inert gas and molecular oxygen at temperatures in the range of 150°–450° C. and thereafter in an inert gas containing no molecular oxygen. The patentees further state that it is preferred to avoid the use of salts which contain sulfate, phosphate or other anions which will leave harmful residues on the catalysts. Suitable salts that may be employed according to this patent are acetates, propionates, butyrates, oxalates, naphthanates nonanoates. The salts of copper, nickel and cobalt in this process are conveniently deposited on the carbon by impregnation of the carbon with solutions of the salt. The catalyst produced in the aforementioned method are useful for the production of hexenes from propylene or octenes from butenes. The catalysts in general provide a method for converting ethylene, propylene and butenes in high yields of straight chain $C_5$ to $C_8$ olefins without the production of appreciable amounts of olefins containing more than 8 carbon atoms. Essentially, then, these catalysts are predominantly dimerization catalysts.

In still another prior art process, the production of a catalyst suitable for olefin oligomerization comprises depositing a cobalt compound capable of yielding cobalt or an oxide of cobalt on heating under the catalyst preparation conditions on activated carbon to form a cobalt/carbon complex; oxidizing the cobalt/carbon complex with molecular oxygen with temperatures in the range of 100°–150° C., and thereafter activating the oxidized cobalt/carbon complex by heating it in an inert atmosphere at temperatures in the range of 150°–550° C. The patentees of this invention state that the process may be carried out more safely than processes using cobalt nitrate as a starting material and suggest that useful salts of cobalt include cobalt formate, cobalt acetate and cobalt isooctoate. This process also discusses that the heating of the cobalt/carbon complex in an inert atmosphere is essential to give catalytic activity to the cobalt/carbon complex.

Also, in British Pat. No. 1,216,272, the use of nickel exchanged X-type molecular sieve zeolites is cited to be a useful catalyst for the dimerization of olefins. The catalyst is prepared by exchanging an X-type molecular sieve zeolite with a nickel salt in an ionic solution of sufficient strength to give substantially complete ion exchange with the molecular sieve, washing the catalyst with an undissociated or a weakly dissociated solvent for the nickel salt until substantially all the excess nickel salt is removed, and finally activating the catalyst by heating in an inert gas between 200° and 800° C. Preferably, according to the patentees of this invention, the exchange is carried by refluxing the molecular sieve with the nickel salt solution.

However, all of the prior art processes discussed above do not provide for a catalyst which produces olefin oligomers rich in linear and slightly branched olefins without the attendant difficulties as described in said prior art processes. It has been found by applicant that an inactive catalyst support in combination with an essentially inactive cobalt oxide on carbon provides an active catalyst system which results in a catalyst capable of oligomerizing alkenes such as propylene at mild conditions to yield olefin oligomers rich in linear and slightly branched olefins containing significant amounts of desirable trimers and tetramers.

By "inactive" is meant that the catalyst supports, namely refractory oxides and molecular sieves, used in this invention do not oligomerize olefins to any extent at the temperatures used in the invention. If any oligomerization should occur, the oligomers would be highly branched. The cobalt oxide on carbon catalysts are likewise "inactive" in that catalysts evidence slow dimerization rates and particularly slow rates in the formation of trimers and tetramers. Physical mixtures of cobalt oxide on carbon and such catalyst supports, however, have been unexpectedly found to increase the rate of formation of dimers, as well as trimers and tetramers. As mentioned above, cobalt oxide on carbon is essentially a dimerization catalyst and the rate of dimerization is a function of the molecular weight of the olefin. That is to say, the higher the molecular weight of the olefin, the slower the rate of dimerization. However, the present invention substantially overcomes this problem in that, when using physical mixtures of the catalyst as per the invention described herein, the rate of dimerization is increased, even for higher molecular weight olefins. While applicant does not wish to be bound by any theory, it is believed that tetramer production from propylene is possible with the catalyst system described by means of the present invention because hexenes are dimerized at an appreciable rate. The trimer of propylene is, therefore, believed to be formed from hexenes and propylene.

SUMMARY OF THE INVENTION

In accordance with the present invention, novel oligomerization catalysts are provided comprising physical mixtures of cobalt oxide on carbon and certain catalyst supports consisting of refractory oxides and molecular sieves. These novel oligomerization catalysts may be prepared by either (a) impregnating activated carbon with a solution containing a cobalt amine complex having the formula $[CoA(NH_3)_4]B$ wherein A is a carbonate or oxalate radical and B is a moiety selected from the group consisting of $CO_3H$, $CO_3NH_4$, $C_2O_4H$ and $C_2O_4NH_4$; followed by decomposing the so impregnated activated carbon at elevated temperature and thereafter admixing the cobalt oxide on carbon with certain support materials such as alumina, bauxite and the like; or (b) by impregnating carbon with cobalt nitrate; adding thereto aqueous sodium hydroxide or potassium hydroxide at room temperature to convert cobalt nitrate to cobalt hydroxide; decomposing the cobalt hydroxide at higher temperatures to cobalt oxide after extracting the sodium or potassium nitrate with water from the mixture and thereafter mixing the cobalt on carbon with a catalyst support as described in (a) above.

These novel catalysts may broadly be described as physical mixtures of cobalt oxide on carbon in combination with certain catalyst supports which can act as proton acceptors and donators. Preferably, the catalyst supports are selected from the group consisting of (1) refractory oxides such as alumina, silica, titantia and the like, including mixtures thereof such as bauxite and (2) crystalline aluminosilicate zeolites, i.e. molecular sieves, which sieves consist substantially of an open framework of $SiO_4$ and $AlO_4$ tetrahedra. Preferably, the catalyst supports of the instant invention comprise alumina containing supports as the catalysts for producing desirable amounts of trimers and tetramers in a propylene oligomerization process.

In addition to applicant's catalyst system providing high yields of $C_9$ and $C_{12}$ linear and slightly branched olefins, it has been found that the olefins produced by means of the oligomerization reaction described herein also contained high concentrations of Type II double bonds. Type II double bonds are unsubstituted internal double bonds such as found in hexene-2 or hexene-3. Type II double bonds are desirable for use in the well-known "oxo" process because they provide high oxonation rates and high yields of alcohol. It has been found that by means of the novel catalyst system provided herein and the oligomerization reaction described herein about 75% of double bonds present and $C_9$ olefins produced are of the Type II as compared with about 20% for prior art processes. Additionally, double bonds present in $C_{12}$ olefins prepared from propylene using the instant catalyst system consists of about 40% type II double bonds as compared with about 20% for the prior art $C_{12}$ olefins made from propylene.

The novel catalysts described above can be prepared in a number of ways. One method involves the impregnation of the activated carbon with a solution containing a cobalt amine complex having the formula $[CoA(NH_3)_4]$ B wherein A is a carbonate or oxalate radical and B is a moiety selected from the group consisting of $CO_3H$, $CO_3NH_4$, $C_2O_4H$ and $C_2O_4NH_4$. Preferred cobalt amine complexes include carbon-atoamine cobalt (III) carbonate and oxalate amine cobalt (III) oxalate while other cobalt ammonia complexes that contain no inorganic anions, such as sulfate, phosphate or chloride may also be used.

In another method of preparation, the activated carbon support is impregnated with cobalt nitrate, to which is added aqueous sodium hydroxide or potassium hydroxide at room temperature thereby converting the cobalt nitrate to cobalt hydroxide. The sodium or potassium nitrate so formed is then extracted with water from the carbon/cobalt hydroxide mixture and the cobalt hydroxide is thereafter decomposed at high temperatures to cobalt oxide. Other cobalt salts that may be employed in this method include cobalt acetate, cobalt formate, cobalt chloride. However, when cobalt chloride is employed, it is essential that the cobalt chloride be completely converted to cobalt hydroxide and that all of the chloride ion is extracted with water.

In still another method, the cobalt nitrate is first converted to cobalt hydroxide and then the cobalt hydroxide is treated with ammonium hydroxide and air before decomposing it at temperatures in the range of from about 250° C. to about 350° C. This method converts some of the divalent cobalt hydroxide to trivalent cobalt hydroxide.

Thereafter, the cobalt on carbon is admixed with certain supports, as mentioned above. Preferably, the cobalt oxide on carbon and catalyst supports are premixed before charging the mixture to a reactor. Preferably, the two solids, i.e., cobalt oxide and carbon and the catalyst support are charged to a dry, stainless steel vessel blanketed with nitrogen and tumbled for 5-6 hours at room temperature.

In a preferred embodiment, illustrating the first method of catalyst preparation described above, about 150 grams of $NH_4HCO_3$ are slurried in 300 ml. distilled water and put into solution with gaseous $NH_3$. To the clear solution is then added 60 grams of $2CoCO_3 \cdot 3Co(OH)_2 \times H_2O$ which is followed by passing a slow stream of gaseous $NH_3$ and $O_2$ into the slurry until the solution is homogeneous. The final solution is dark red in color and contains about 0.00125 moles of Co/ml. in a large excess of dissolved $NH_3$. Thereafter, 50 mls. of this solution, which contains carbonatoamine cobalt (III) carbonate, is poured over 40 g. of activated carbon. A portion of the water is driven off by blowing a stream of hot air over same until carbon appears dry. The partly dried carbon is then heated under vacuum (1 mm) to 350° C. for approximately one-half hour, and, after cooling the carbon to room temperature, it is blanketed with nitrogen.

Illustrating the second method of catalyst preparation, about 4 g. of activated carbon is impregnated with about 15 g. $Co(NO_3)_2 \cdot 6H_2O$ dissolved in 30 ml. of distilled water. A portion of the water is driven off by blowing a hot air stream over same until carbon appears dry. The temperature of the carbon is kept below about 60° C. Thereafter, about 6 g. of KOH or NaOH dissolved in 60 ml. distilled water is poured over the carbon and allowed to sit for a period of about 12 hours, accompanied by occasional light agitation. The entire mixture is transferred to a Soxhlet extractor and extracted with hot water for 24 hours to remove $KNO_3$. To assure that trivalent cobalt is present, the $Co(OH)_2$ on carbon is wetted with 50 ml. of $NH_4OH$ and oxidized by passing a stream of air or oxygen saturated with $NH_3$ and $H_2O$ over the carbon cobalt hydroxide at room temperature for about 24 hours. To convert the cobalt hydroxide into cobalt oxide, the web carbon cobalt hydroxide mixture is slowly heated for about ½ hour to 275° under about 1 mm vacuum and is kept at 275° C. for 2 hours.

The novel catalysts prepared by the abovedescribed methods will normally contain from about 0.5 to about 20.0 weight % cobalt oxide on carbon, preferably from about 5 to about 15 weight %, most preferably from about 5 to about 12 weight %. The ratio of cobalt oxide on carbon to the catalyst supports of the instant invention is preferably in the range of from about 1:100 to about 100:1, more preferably from about 10:1 to about 1:10, most preferably from 2:1 to about 1:6.

As discussed above, the novel catalysts prepared in the afore-described manner are useful as oligomerization catalysts such that propylene can be oligomerized to linear and slightly branched olefins in high yields containing desirable amounts of trimers and tetramers.

The conditions for polymerizing olefins such as propylene with a catalyst system described by the invention herein includes the temperatures in the range of from about 0° to about 250° C. preferably from about 50° to about 150° C. Pressures may vary widely from 1 to 100 atmospheres and will ultimately depend on the temperature of polymerization and the boiling point of the olefin and diluent, if one is used. Liquid hourly space velocities (LHSV) employed are a function of the conversion desired and may be in the range of from about 0.1 to about 20 LHSV preferably from about 0.2 to about 5.0.

The olefins that may be oligomerized by use of the novel catalysts of the present invention include propylene, ethylene, butene, and the like. In a broader application, these novel catalysts can be employed to polymerize olefins such as alkenes, having from 2 to 8 carbon atoms and mixtures thereof.

The invention will be further understood, but is not to be so limited, by reference to the following Example:

EXAMPLE 1

In this example, batch-type runs were employed to obtain the results set forth in Table I. The procedure included charging premixed cobalt oxide on carbon and the various catalyst supports (as set forth in Table I) under nitrogen to a dry 2 liter stainless steel autoclave at room temperature and atmospheric pressure. The autoclave was sealed and a measured volume (see Table I) of liquid propylene, dried over a molecular sieve, was charged to the autoclave at room temperature. The agitator was started and heat applied to quickly (about 15 minutes) bring the olefin and catalyst mixture to the desired temperature. After the desired residence time the reaction mixture was quickly cooled in less than 5 minutes to room temperature by running chilled water through the cooling coil inside the autoclave. The unreacted olefin was quickly bled off through a wet test meter and the catalyst and reaction product withdrawn from the bottom of the autoclave and run into a tared glass receiver containing a fritted disk. The autoclave was washed twice with 100 ml. of n-heptane which was added to the receiver containing the product and catalyst. The total amount recovered was weighed and most of the n-heptane and liquid product separated from the catalyst by means of the fritted disk in the receiver. The liquid product and n-heptane were distilled through a spinning band column and separated into $C_6$, $C_9$, $C_{12}$ and higher olefin fractions which were analyzed by GC and olefin type analysis by infrared. Olefins and n-heptane which remained adsorbed on the solid catalyst were removed by stripping the catalyst under vacuum between 25°–100° C. until catalyst weight remaining constant.

The results of several polymerization runs are found in attached Table I. These results clearly demonstrate that by combining an essentially inactive cobalt oxide on carbon with an inactive catalyst support, an active catalyst system results which is capable of polymerizing propylene at mild conditions to yield oligomers rich in linear and slightly branched olefins.

TABLE I

| | OLIGOMERIZATION OF PROPYLENE AT 85° C. | | | | | | |
|---|---|---|---|---|---|---|---|
| Run No. 1- | A | B | C | D | E | F | G |
| Propylene charged, g | 49 | 143 | 165 | 165 | 180 | 180 | 3268.3 |
| Reaction Time, Hrs. | 5 | 5 | 5 | 5 | 2 | 5 | 175 |

TABLE I-continued

OLIGOMERIZATION OF PROPYLENE AT 85° C.

| | | | | | | | |
|---|---|---|---|---|---|---|---|
| Pressure, PSIG | 350 | 420 to 325 | 420 to 350 | 375 to 290 | 340–300 | 400–350 | 460–380 |
| Catalyst | 7.5 g of 7.5 wt.% $Co_3O_4$ on Carbon | 17 g of 75 wt.% $Co_3O_4$ on Carbon +100 g 5A Molecular sieve (g) | 19.5 g of 11 wt.% $Co_3O_4$ on Carbon + 121 g Porocel (c) (g) | 14.2 g of 7.5 wt.% $Co_3O_4$ on Carbon + 121 g Porocel (d)(g) | 17.7 g of 7.5 wt.% $Co_3O_4$ on Carbon + 121 g Porocel (c)(g) | 20.9 g of 6.9 wt.% $Co_3O_4$ on Carbon + 50 g Porocel (d)(g) | 21.0 g of 7.5 wt.% $Co_3O_4$ on Carbon (d) |
| Conversion, wt.% | 20 | 43.8 | 66.2 | 63.0 | 62.0 | 53.3 | 40.0 |
| Selectivity to, wt.% | | | | | | | |
| $C_6$ | 91.2 | 78.5 | 43.3 | 43.0 | 67.6 | 67.7 | 49.2 |
| $C_9$ | 8.6 | 18.3 | 21.5 | 23.5 | 14.0 | 18.2 | 10.8 |
| $C_{12}$ | 0.2 | 3.1 | 27.8 | 30.4 | 18.4 | 14.1 | 3.4 |
| $C_{12+}$ | — | — | 7.4 | 3.0 | — | — | — |
| Compositions, wt.% | | | | | | | |
| n-Hexenes | 49.7 | 54.0 | 65.8 | 63.6 | 54.5 | 54.6 | 49.2 |
| $C_6$ Methylpentenes | 50.1 | 45.7 | 34.0 | 35.5 | 45.0 | 45.0 | 48.6 |
| DiMethylbutenes | 0.2 | 0.3 | 0.3 | 0.9 | 0.5 | 0.4 | 2.2 |
| n-Nonenes | 10.6 | 16.2 | 15.1 | 9.3 | 11.3 | 12.2 | 16.0 |
| Methyloctenes (e) | 48.6 | 49.1 | 29.7 | 22.1 | 33.7 | 34.6 | 47.7 |
| $C_9$ DiMethylheptenes | 35.8 | 29.3 | 18.8 | 14.2 | 40.4 | 38.8 | 34.0 |
| Unidentified | 5.0 | 5.4 | 33.1(f) | 54.4(f) | 14.6 | 14.4 | 2.3 |

(a) Activated carbon, 12×30 mesh. Cobalt oxide put on carbon by decomposing divalent cobalt hydroxide containing some trivalent cobalt.
(b) Activated carbon, 14×40 mesh. Cobalt oxide put on carbon as under (a). 5A Molecular sieve was dried at 450° C. for two hours before using it.
(c) Activated carbon, 14×40 mesh. Cobalt oxide put on carbon as under (a). Porocel is activated bauxite. It was dried at 450° C. for 2 hours.
(d) Activated carbon, 14×40 mesh. Cobalt oxide put on carbon by decomposing carbonatoamine cobalt (III) carbonate.
(e) Methyloctenes consist mostly of 2- and 4-methyloctenes.
(f) Unidentified $C_9$ olefins contain some ethylheptenes.
(g) At the conditions employed in the runs both Porocel and 5A molecular sieve gave no reaction with propylene.

What is claimed is:

1. A method of preparing alkene oligomerization catalysts which comprises:
   a. impregnating activated carbon with a solution of cobalt amine complexes having the generic formula $[CoA(NH_3)_4]B$ where A is a carbonate or oxalate radical and B is a moiety selected from the group consisting of $CO_3H$, $CO_3NH_4$, $C_2O_4H$ and $C_2O_4NH$;
   b. decomposing said activated carbon impregnated with said cobalt amine complexes at temperatures of between about 250° to about 350° C. to produce cobalt oxide on carbon; and thereafter,
   c. admixing said cobalt oxide on carbon with a refractory oxide as a catalyst support.

2. The method of claim 1 wherein the refractory oxide contains alumina.